US00PP24562P2

(12) United States Plant Patent
Bauer

(10) Patent No.: US PP24,562 P2
(45) Date of Patent: Jun. 17, 2014

(54) ***COREOPSIS* 'MAIN STREET'**

(50) Latin Name: *Coreopsis verticillata*
Varietal Denomination: Main Street

(71) Applicant: Patricia M. Bauer, Lucinda, PA (US)

(72) Inventor: Patricia M. Bauer, Lucinda, PA (US)

(73) Assignee: ItSaul Plants, LLC, Alpharetta, GA (US)

( * ) Notice: Subject to any disclaimer, the term of this patent is extended or adjusted under 35 U.S.C. 154(b) by 107 days.

(21) Appl. No.: 13/573,636

(22) Filed: Sep. 27, 2012

(51) Int. Cl.
*A01H 5/00* (2006.01)

(52) U.S. Cl.
USPC ..... Plt./417

(58) Field of Classification Search
USPC ..... Plt./417
See application file for complete search history.

*Primary Examiner* — Annette Para
(74) *Attorney, Agent, or Firm* — Penny J. Aguirre

(57) ABSTRACT

A new cultivar of *Coreopsis verticillata* named 'Main Street', characterized by its ray florets that are burgundy red in color with occasional flecks and spots of white near the tips on the upper surface when mature and greyed-yellow and diffused with reddish-purple near the base on the lower surface, its *C. verticillata* type foliage, its cold hardiness to at least U.S.D.A. Zone 5, its continuous blooms from late May/early June until frost, its height of 45 to 60 cm and an average spread of 45 cm, and its vigorous growth habit and ability to propagate well under greenhouse conditions in winter.

2 Drawing Sheets

Botanical classification: *Coreopsis verticillata.*
Variety denomination: 'Main Street'.

BACKGROUND OF THE INVENTION

The present invention relates to a new and distinct cultivar of *Coreopsis* plant, botanically known as *Coreopsis verticillata* 'Main Street' and will be referred to hereinafter by its cultivar name, 'Main Street'. The new cultivar of *Coreopsis* is an herbaceous perennial grown for landscape and container use.

The new invention arose as a naturally occurring whole plant mutation in the Inventor's garden in Lucinda, Pa. in summer of 2009. The parent plants of 'Main Street' are unknown.

Asexual reproduction of the new cultivar was first accomplished by stem tip cutting under the direction of the Inventor in Alpharetta, Ga. in October of 2010. The characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'Main Street' as unique from all *Coreopsis* cultivars known to the Inventor.

1. 'Main Street' exhibits ray florets that are burgundy red in color with occasional flecks spots and of white near the tips on the upper surface when mature and greyed-yellow and diffused with reddish-purple near the base on the lower surface.
2. 'Main Street' exhibits *C. verticillata* type foliage.
3. 'Main Street' has shown to be hardy at least in U.S.D.A. Zone 5.
4. 'Main Street' blooms continuously from late May/early June until frost in Pennsylvania.

5. 'Main Street' exhibits a height of 45 to 60 cm (18 to 24 inches) and an average spread of 45 cm (18 inches).
6. 'Main Street' exhibits a vigorous growth habit and propagates well under greenhouse conditions in winter.

'Main Street' can be most closely compared to *Coreopsis* cultivars 'Route 66' (U.S. Plant Pat. No. 20,609) and 'Limerock Ruby' (U.S. Plant Pat. No. 15,455). 'Route 66' is similar to 'Main Street' in being easily propagated over winter and in having a long blooming habit. 'Route 66' differs from 'Main Street' in having ray florets that change from being yellow in color with a prominent burgundy eye and becoming almost solid burgundy when they mature and in being 4 to 6 inches taller in height. 'Limerock Ruby' is similar to 'Main Street' in having a comparable flower color. 'Limerock Ruby' differs from 'Main Street' in being hardy only to U.S.D.A. Zone 8 and in being shorter in height.

BRIEF DESCRIPTION OF THE DRAWING

The accompanying colored photographs illustrate the overall appearance and distinct characteristics of the new *Coreopsis* as grown in Alpharetta, Ga. The photographs were taken of plants about one year in age as grown in a 2-gallon container without deadheading.

The photograph in FIG. 1 provides a side view of 'Main Street' in bloom.

Figure 1:
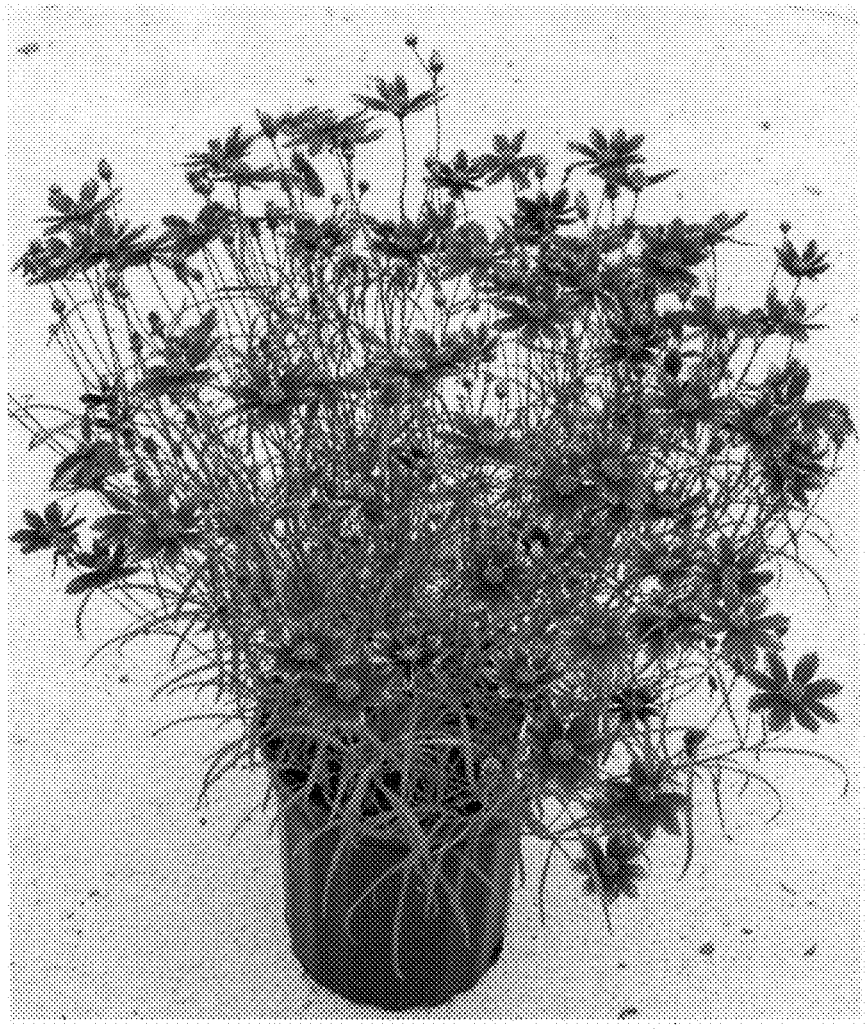
Figure 2:
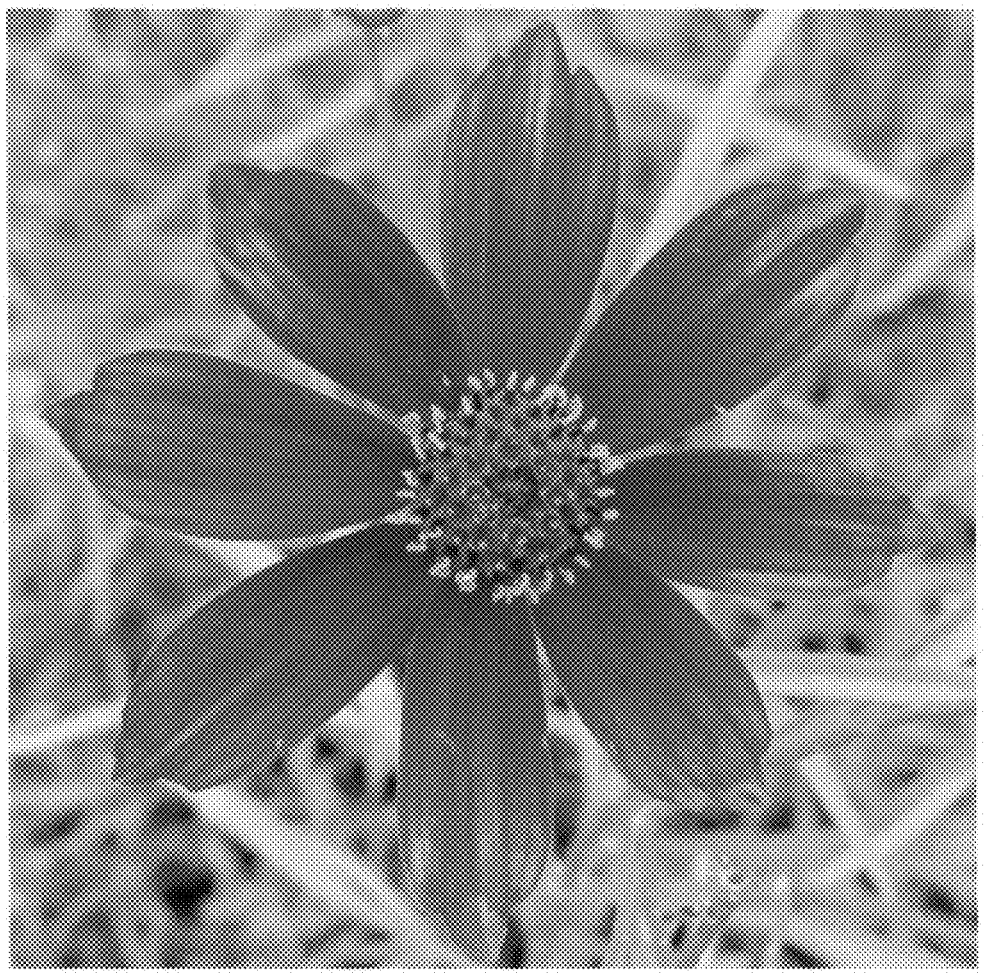

The photograph in FIG. 2 provides a close-up view of an inflorescence of 'Main Street'. The colors in the photograph may differ slightly from the color values cited in the detailed botanical description, which accurately describe the colors of the new *Coreopsis.*

DETAILED BOTANICAL DESCRIPTION

The following is a detailed description of the new cultivar as observed on plants about one year in age as grown in 2-gallon containers in Alpharetta, Ga. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Blooms from late May/early June until Frost in Pennsylvania.

*Plant habit*.—Herbaceous perennial, densely clump-forming with numerous basal branching to produce a bushy habit.

*Height and spread*.—Reaches a height of 45 to 60 cm (18 to 24 inches) and an average spread of 45 cm (18 inches).

*Cold hardiness*.—At least in U.S.D.A Zone 5.

*Diseases resistance*.—No particular resistance or susceptibility has been observed.

*Root description*.—Fibrous, fine and well-branched.

Growth and propagation:

*Propagation*.—Terminal stem cuttings.

*Growth rate*.—Vigorous and grows well under greenhouse conditions in winter.

Stem description:

*Shape*.—Rounded, solid.

*Stem color*.—Immature stems; 144B, mature stems; 144A.

*Stem size*.—An average of 45 cm in length and 2 mm in width.

*Stem surface*.—Glabrous, satin finish, slightly ridged.

*Branching habit*.—An average of 70 basal branches.

Foliage description:

*Leaf division*.—Simple.

*Leaf margins*.—Deeply incised, typically tri-lobed.

*Leaf size*.—Up to 7 cm in length and 3.5 cm in width, lobes an average of 2 cm in length and 2 mm in width.

*Leaf shape*.—Fan shaped overall, lobes narrowly linear.

*Leaf base*.—Attenuate.

*Leaf apex*.—Acute.

*Leaf venation*.—Pinnate, not prominent, matches leaf color on both surfaces.

*Leaf attachment*.—Sessile.

*Leaf arrangement*.—Opposite.

*Leaf internode length*.—Average of 4.5 cm.

*Leaf quantity*.—An average of 12 per stem.

*Leaf surface*.—Glabrous.

*Leaf color*.—New growth and mature growth upper and lower surface; 144A.

*Leaf fragrance*.—Moderate and slightly sweet when crushed.

Flower description:

*Inflorescence type*.—Composite with ray florets surrounding disk florets in the center forming a radiant head, inflorescences born at nodes and terminus.

*Lastingness of inflorescence*.—About one week until senescence of ray flowers, bracts and disk flowers are persistent.

*Fragrance*.—None detected.

*Quantity of inflorescences*.—An average of 7 per stem open at one time with new blooms opening until frost.

*Inflorescence size*.—An average of 5 mm in depth and up to 4.5 cm in width with disk portion an average of 9 mm in diameter.

*Inflorescence buds*.—Average of 4 mm in depth and 5 mm in width, shape is oblate, color is 151A with base 137B and apex a color between 154A and 154B.

*Peduncle*.—Average of 5 cm in length and 1 mm in diameter, 144A in color, glabrous surface.

Involucral bracts:

*Bract number*.—Outer bracts; average of 6, inner bracts; 8.

*Bract arrangement*.—Outer bracts are un-fused spreading and held at 45° from perpendicular, inner bracts overlap and surround receptacle with a campanulate form and held close to ray florets with apical portion spreading outward.

*Bract size*.—Outer bracts about 3 mm in length and 1 mm in width, inner bracts about 6 mm in length and 4 mm in width with free portion an average of 2 mm in length and 2 mm in width.

*Bract color*.—Outer bracts 137B with thin margin of 145A (both surfaces), inner bracts 143A and blending to 164A at apex (both surfaces).

*Bract texture*.—Outer bracts glabrous and satiny on both surfaces, inner bracts glabrous and waxy on both surfaces.

*Bract apex*.—Acute (inner and outer).

*Bract base*.—Truncate (inner and outer).

*Bract shape*.—Outer bracts linear, inner bracts triangular.

Ray florets (sterile):

*Number*.—8.

*Shape*.—Oblong/oblanceolate.

*Size*.—Average of 2 cm in length and 7 mm in width.

*Apex*.—Typically 2-notched with center slightly protruding.

*Base*.—Cuneate.

*Margins*.—Entire except for apex.

*Aspect*.—Held nearly horizontal to slightly upward.

*Surface*.—Glabrous and ridged on both surfaces.

*Color*.—Upper surface when opening; a blend of 187A and 187B, lower surface when opening; 164D and suffused at base with 187A with a fine margin of 187A, upper surface when mature; a color between 187B and 59A with tips spotted with NN155B, lower surface when mature; 161D and suffused at base with 187C.

Disk flowers (male and female):

*Number*.—Numerous, about 80.

*Shape*.—Tubular, corolla is fused, flared at apex.

*Size*.—About 4 mm in length and 1 mm in width.

*Color*.—Immature and mature; outer edges 25A blending into center and becoming N163C, in masse: with stigmas 200B, corolla; 22A and apex 11C and transparent.

*Receptacle*.—About 4 mm in diameter and 2 mm in depth, N137A in color.

Reproductive organs:

*Presence*.—Disk flowers are perfect, ray flowers are sterile.

*Gynoecium*.—1 Pistil, 5 mm in length, style is very fine and about 23A in color and translucent, bifid pilose stigma is 172A in color with branches about 1 mm in length and recurved, ovary is 1 mm in length, 1 mm in width, inferior, and 150B in color.

*Androcoecium.*—2 stamens, fused into tube surrounding style, 2 mm in length and 0.5 mm in width, about 200A in color, scarce amount of pollen N163C in color.

*Fruit/seed.*—Seed pods; oblong in shape, slightly curved with narrow wings, about 8.5 mm in length and 3 mm in width, a blend of 199A and 200A in color, seeds; 20 to 30 per pod, about 4.5 mm in length and 1.5 mm in width, 200A in color.

It is claimed:

1. A new and distinct cultivar of *Coreopsis* plant named 'Main Street' as herein illustrated and described.

* * * * *